(12) United States Patent
Luber et al.

(10) Patent No.: US 7,323,192 B2
(45) Date of Patent: Jan. 29, 2008

(54) IMMEDIATE RELEASE TABLET

(75) Inventors: Joseph Luber, Quakertown, PA (US); Frank J. Bunick, Randolph, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/966,493

(22) Filed: Sep. 28, 2001

(65) Prior Publication Data

US 2003/0068373 A1    Apr. 10, 2003

(51) Int. Cl.
A61K 9/20    (2006.01)

(52) U.S. Cl. ........................ 424/464; 424/465

(58) Field of Classification Search ............... 424/465, 424/484, 464, 479, 472, 489, 400, 468, 469, 424/470, 471
See application file for complete search history.

(56) References Cited

U.S. PATENT DOCUMENTS

| | | | |
|---|---|---|---|
| 582,438 A | 5/1897 | Scheidler | |
| 599,865 A | 3/1898 | Richards | |
| 2,307,371 A | 1/1943 | Hileman | |
| 2,996,431 A | 8/1961 | Barry | |
| 3,085,942 A | 4/1963 | Magid et al. | |
| 3,108,046 A * | 10/1963 | Harbit ........................ 424/470 | |
| 3,146,169 A | 8/1964 | Stephenson et al. | |
| 3,627,583 A | 12/1971 | Troy et al. | |
| 3,726,622 A | 4/1973 | DeTroyer et al. | |
| 3,804,570 A | 4/1974 | Hoschele et al. | |
| 3,832,252 A | 8/1974 | Higuchi et al. | |
| 4,076,819 A | 2/1978 | Maffrand | |
| 4,097,606 A | 6/1978 | Chavkin et al. | |
| 4,139,589 A | 2/1979 | Beringer et al. | |
| 4,230,693 A | 10/1980 | Izzo et al. | |
| 4,271,206 A | 6/1981 | Fariel et al. | |
| 4,273,793 A | 6/1981 | Fariel et al. | |
| 4,292,017 A | 9/1981 | Doepel | |
| 4,362,757 A | 12/1982 | Chen et al. | |
| 4,372,942 A | 2/1983 | Cimiluca | |
| 4,392,493 A | 7/1983 | Niemeijer | |
| 4,425,332 A | 1/1984 | James | |
| 4,473,526 A | 9/1984 | Buhler et al. | |
| 4,518,335 A | 5/1985 | Pujari | |
| 4,528,335 A | 7/1985 | Selby et al. | |
| 4,533,345 A | 8/1985 | Louw | |
| 4,544,345 A | 10/1985 | Buhler et al. | |
| 4,569,650 A | 2/1986 | Kramer | |
| 4,661,521 A | 4/1987 | Salpeckar et al. | |
| 4,665,116 A * | 5/1987 | Kornhaber et al. ......... 524/268 | |
| 4,686,212 A | 8/1987 | Ducatman et al. | |
| 4,749,575 A | 6/1988 | Rotman | |
| 4,757,090 A | 7/1988 | Salpeckar et al. | |
| 4,762,719 A | 8/1988 | Forester | |
| 4,781,714 A | 11/1988 | Eckenhoff et al. | |
| 4,813,818 A | 3/1989 | Sanzone | |
| 4,820,524 A | 4/1989 | Berta | |
| 4,851,226 A | 7/1989 | Julian et al. | |
| 4,882,167 A | 11/1989 | Jang | |
| 4,894,234 A * | 1/1990 | Sharma et al. ............... 424/440 |
| 4,894,236 A | 1/1990 | Jang et al. | |
| 4,929,446 A | 5/1990 | Bartolucci | |
| 4,965,027 A | 10/1990 | Takahashi | |
| 4,980,169 A | 12/1990 | Oppenheimer et al. | |
| 5,002,970 A | 3/1991 | Eby, III | |
| 5,030,447 A * | 7/1991 | Joshi et al. .................. 514/510 |
| 5,059,112 A | 10/1991 | Wieser | |
| 5,075,114 A | 12/1991 | Roche | |
| 5,089,270 A | 2/1992 | Hampton et al. | |
| 5,098,715 A * | 3/1992 | McCabe et al. ............. 424/479 |
| 5,145,868 A | 9/1992 | von Sprecher et al. | |
| 5,146,730 A | 9/1992 | Sadek et al. | |
| 5,169,645 A | 12/1992 | Shukla et al. | |
| 5,188,840 A | 2/1993 | Iida et al. | |
| 5,200,191 A | 4/1993 | Steele et al. | |
| 5,213,738 A | 5/1993 | Hampton et al. | |
| 5,213,808 A | 5/1993 | Bar-Shalom et al. | |
| 5,228,916 A | 7/1993 | Berta | |
| 5,229,164 A | 7/1993 | Pins et al. | |
| 5,368,863 A | 11/1994 | Eckenhoff et al. | |
| 5,391,378 A | 2/1995 | Sanderson | |
| 5,405,642 A | 4/1995 | Gilis et al. | |
| 5,415,868 A | 5/1995 | Smith et al. | |
| 5,436,026 A | 7/1995 | Berta | |
| 5,456,920 A | 10/1995 | Matoba et al. | |
| 5,459,983 A | 10/1995 | Sadek et al. | |
| 5,464,631 A | 11/1995 | Hoover et al. | |

(Continued)

FOREIGN PATENT DOCUMENTS

DE    19954420 A1    5/2001

(Continued)

OTHER PUBLICATIONS

Hawley's Condensed Chemical Dictionary, 12th Edition, 1993, pp. 960-961.*

(Continued)

Primary Examiner—S. Tran

(57) ABSTRACT

An immediate release tablet is provided. The tablet comprises at least 60 weight % of an active ingredient and powdered wax having a melting point greater than about 90° C. The tablet may advantageously be produced by direct compression. Although the wax is hydrophobic, the tablet has excellent disintegration.

9 Claims, No Drawings

U.S. PATENT DOCUMENTS

| | | | | |
|---|---|---|---|---|
| 5,489,436 | A | 2/1996 | Hoy et al. | |
| 5,494,681 | A * | 2/1996 | Cuca et al. | 424/484 |
| 5,511,361 | A | 4/1996 | Sauter | |
| 5,538,125 | A | 7/1996 | Berta | |
| 5,578,336 | A | 11/1996 | Monte | |
| 5,609,010 | A | 3/1997 | Sauter | |
| 5,614,207 | A | 3/1997 | Shah et al. | |
| 5,643,984 | A * | 7/1997 | Mueller et al. | 524/272 |
| 5,679,406 | A | 10/1997 | Berta | |
| 5,681,583 | A * | 10/1997 | Conte et al. | 424/472 |
| 5,681,584 | A | 10/1997 | Savastano et al. | |
| 5,711,961 | A | 1/1998 | Reiner et al. | |
| 5,795,588 | A | 8/1998 | Sauter | |
| 5,807,579 | A | 9/1998 | Vilkov et al. | |
| 5,824,338 | A | 10/1998 | Jacobs et al. | |
| 5,827,874 | A | 10/1998 | Meyer et al. | |
| 5,830,501 | A | 11/1998 | Dong et al. | |
| 5,830,502 | A | 11/1998 | Dong e al. | |
| 5,834,035 | A | 11/1998 | Osada et al. | |
| 5,837,301 | A | 11/1998 | Arnott et al. | |
| 5,853,760 | A | 12/1998 | Cremer | |
| 5,871,781 | A | 2/1999 | Myers et al. | |
| 5,942,034 | A | 8/1999 | Brehant et al. | |
| 5,997,905 | A | 12/1999 | McTeigue et al. | |
| 6,001,391 | A | 12/1999 | Zeidler et al. | |
| 6,099,859 | A * | 8/2000 | Cheng et al. | 424/464 |
| 6,103,257 | A | 8/2000 | Nisonoff | |
| 6,117,479 | A | 9/2000 | Hogan et al. | |
| 6,120,802 | A | 9/2000 | Breitenbach et al. | |
| 6,149,939 | A | 11/2000 | Strumor et al. | |
| 6,149,943 | A | 11/2000 | McTeigue et al. | |
| 6,194,000 | B1 * | 2/2001 | Smith et al. | 424/458 |
| 6,200,590 | B1 | 3/2001 | Eley | |
| 6,217,907 | B1 | 4/2001 | Hunter et al. | |
| 6,248,760 | B1 | 6/2001 | Wilhelmsen | |
| 6,270,790 | B1 * | 8/2001 | Robinson et al. | 424/441 |
| 6,350,398 | B1 | 2/2002 | Breitenbach et al. | |
| 6,365,185 | B1 | 4/2002 | Ritschel et al. | |
| 6,372,254 | B1 * | 4/2002 | Ting et al. | 424/473 |
| 6,433,015 | B1 | 8/2002 | Meyer | |
| 6,727,213 | B2 | 4/2004 | Waschenbach et al. | |
| 6,730,646 | B1 | 5/2004 | Waschenbach et al. | |
| 2001/0001280 | A1 | 5/2001 | Dong et al. | |
| 2002/0028240 | A1 | 3/2002 | Sawada et al. | |
| 2002/0082299 | A1 | 6/2002 | Meyer | |
| 2003/0203016 | A1 | 10/2003 | Suwelack | |
| 2003/0224043 | A1 * | 12/2003 | Appel et al. | 424/465 |

FOREIGN PATENT DOCUMENTS

| | | | |
|---|---|---|---|
| EP | 0 088 556 B1 | 9/1983 | |
| EP | 0 239 983 B1 | 10/1987 | |
| EP | 0 294 993 B1 | 12/1988 | |
| EP | 0 387 885 A2 | 9/1990 | |
| EP | 0 387 885 B1 | 9/1990 | |
| EP | 0 455 599 A1 | 11/1991 | |
| EP | 0 481 547 A1 | 4/1992 | |
| EP | 0 531 524 B1 | 3/1993 | |
| EP | 0 572 731 A1 | 12/1993 | |
| EP | 0 610 854 A | 8/1994 | |
| EP | 0 646 650 A2 | 4/1995 | |
| EP | 0 646 650 A3 | 3/1996 | |
| EP | 0 740 938 A2 | 11/1996 | |
| EP | 0 619 854 B1 | 3/1998 | |
| EP | 0 834 516 B1 | 4/1998 | |
| EP | 0 861 659 A1 | 9/1998 | |
| EP | 0 864 324 A | 9/1998 | |
| EP | 1 077 065 A1 | 2/2001 | |
| EP | 0 950 402 B1 | 5/2003 | |
| EP | 0 788 790 B1 | 5/2004 | |
| GB | 866 681 | 4/1961 | |
| GB | 866 681 A | 4/1961 | |
| GB | 888 038 | 1/1962 | |
| GB | 936 386 | 9/1963 | |
| GB | 994 742 | 6/1965 | |
| GB | 1 144 915 | 3/1969 | |
| GB | 1 372 040 | 10/1974 | |
| GB | 1 464 388 | 2/1977 | |
| GB | 1 510 772 | 5/1978 | |
| GB | 2 182 559 A | 5/1987 | |
| GB | 2 197 778 A | 6/1988 | |
| GB | 2 284 760 A | 6/1995 | |
| NL | 8602556 | 5/1988 | |
| WO | WO94/06416 A1 | 3/1994 | |
| WO | WO94/07470 A1 | 4/1994 | |
| WO | WO95/02396 A1 | 1/1995 | |
| WO | WO97/06695 A1 | 2/1997 | |
| WO | WO98/20870 A1 | 5/1998 | |
| WO | WO99 00122 A1 | 1/1999 | |
| WO | WO99/02136 A1 | 1/1999 | |
| WO | WO99/32092 | 7/1999 | |
| WO | WO99/32092 A1 | 7/1999 | |
| WO | WO99/51209 A1 | 10/1999 | |
| WO | WO99/56730 A1 | 11/1999 | |
| WO | WO 00/18447 A2 | 4/2000 | |
| WO | WO 00/18447 A3 | 4/2000 | |
| WO | WO 00 25755 A | 5/2000 | |
| WO | WO 00/25755 A1 | 5/2000 | |
| WO | WO 01/21155 A1 * | 3/2001 | |
| WO | WO 02/19833 A2 | 3/2002 | |
| WO | WO 02/19833 A3 | 3/2002 | |

OTHER PUBLICATIONS

Webster's II, New Colllege Dictionary, p. 691.*

Lachman et al. "The Theory and Practice of Industrial Pharmacy," Chapter II, (3rd Ed. 1986).

Lieberman et al., "Pharmaceutical Dosage Forms—Tablets" vol. 2, 2nd Ed, Marcel Kekker, Inc. 1990. pp. 213-217; 327-329.

C. De Brabander et al., "Marix mini-tablets based on starch/microcrystalline wax mixtures", International Journal of Pharmaceutics, Netherlands Apr. 20, 2000, vol. 199, No. 2, pp. 195-203 XP002233674.

PCT Search Report for PCT/US 02/30613 dated Mar. 17, 2003.

Catellani, P.L. et al., "Centrifugal die filling system in a new rotary tablet machine", International Journal of Pharmaceutics, 88 (1992), pp. 285-291.

Cuff, George et al., "A Preliminary Evaluation of Injection Molding as a Technology to Produce Tablets", Pharmaceutical Technology (1998), Jun. 1998, pp. 96-106.

Lachman, Leon et al., "Chapter II—Tablets", The Theory and Practice of Industrial Pharmacy, (1986), pp. 293-345.

* cited by examiner

IMMEDIATE RELEASE TABLET

The present invention relates to an immediate release tablet comprising an active ingredient and powdered wax.

BACKGROUND OF THE INVENTION

Certain pharmaceutically active ingredients, such as analgesics, must be employed in relatively high doses to be therapeutically effective. Acetaminophen, for example, is commonly used at 1000 mg per dose, divided into two tablets containing 500 mg each. Formulating high levels of an active ingredient into a tablet that remains small enough for a consumer to swallow comfortably is a challenge. This is complicated by the fact that most active ingredients will not by themselves readily compress into a tablet. Accordingly, they are mixed with inactive excipients that form bonds under compression to hold the tablet together. One common method of accomplishing this is by wet granulation, in which the active ingredient and an aqueous solution of a binder (such as starch paste) are mixed and granulated. The resulting material is suitable for compression into tablets.

More recently, direct compression of dry blends has gained favor in the pharmaceutical industry due to the economics of eliminating wet granulation and its accompanying drying operations. Direct compression is useful for active ingredients that are highly potent. However, the relatively high amount of low potency active ingredients required in a dosage form makes them poor candidates for direct compression into tablets.

Workers in the field have attempted to overcome this problem. For example, U.S. Pat. Nos. 4,661,521 and 4,757,090 to Salpekar et al. relate to an N-acetyl-p-aminophenol (acetaminophen) composition capable of being directly formed into a tablet, comprising acetaminophen, a pharmaceutically acceptable pregelatinized starch, a pharmaceutically acceptable lubricant, water and optionally an auxiliary binder such as polyvinylpyrrolidone. These compositions are prepared by wet granulation using an aqueous starch slurry.

U.S. Pat. No. 4,882,167 to Jang describes a controlled and continuous release matrix for tablets or implants of biologically active agents. The matrix comprises a hydrophobic carbohydrate polymer such as ethyl cellulose, and optionally at least one digestive-difficulty soluble component such as wax, fatty acid material or a neutral lipid.

U.S. Pat. No. 5,169,645 to Shukla et al. relates to directly compressible, wax-containing granules useful as a particulate drug diluent. The granules are made by admixing in the melted state one or more pharmaceutically acceptable waxes with one or more flow improving additives, cooling the mixture and then granulating. The resulting wax-containing granules can be compressed into matrices containing an active ingredient.

PCT Application WO 99/32092 discloses a method for the manufacture of tablets that disperse easily and quickly in the oral cavity. The method comprises preparing a dry granulation of one or more medicaments blended with suitable excipients, flavors and a combination of a waxy material and phospholipid or an intense sweetener for taste-masking and compressing into tablets. The resulting tablets comprise 1 to 60 parts of the medicament.

U.S. Pat. No. 5,456,920 to Matoba et al. describes a compression-moldable composition comprising an active ingredient, an excipient, and an oily or fatty substance having a lower melting point of about 20° to 90° C.

It has now been discovered that an immediate release tablet can be made from a mixture comprising at least 60 weight % active ingredient(s) and a powdered wax having a melting point of greater than about 90° C. Although the powdered wax is hydrophobic, the tablets have excellent disintegration, and meet the USP dissolution specifications for immediate release tablets containing the active ingredient. Rapid onset of therapeutic action is a desirable feature, especially for analgesics.

SUMMARY OF THE INVENTION

The invention provides an immediate release tablet comprising at least 60 weight % of an active ingredient and a powdered wax having a melting point greater than about 90° C., said tablet meeting the USP dissolution specifications for immediate release tablets containing said active ingredient.

DETAILED DESCRIPTION OF THE INVENTION

The tablet comprises at least one active ingredient. Suitable active ingredients broadly include pharmaceutically active ingredients, dietary supplements, nutritionals, nutriceuticals, and the like. More specifically these include analgesics, anti-inflammatory agents, decongestants, expectorants, antitussives, antihistamines, gastrointestinal agents, diuretics, bronchodilators, sleep-inducing agents, vitamins (such as vitamin D and vitamin K), minerals (such as calcium and magnesium), anti-infectives, nutrients, and mixtures thereof. The active ingredient may be selected for example from acetaminophen, ibuprofen, ketoprofen, flurbiprofen, naproxen, diclofenac, rofecoxib, celecoxib, aspirin, pseudoephedrine, phenylpropanolamine, chlorpheniramine, dextromethorphan, diphenhydramine, dimenhydrinate, meclizine, famotidine, loperamide, ranitidine, cimetidine, bisacodyl, psyllium, astemizole, loratadine, desloratadine, fexofenadine, cetirizine, antacids, mixtures thereof and pharmaceutically acceptable salts or metabolites thereof. Most preferably, the active ingredient is selected from the group consisting of acetaminophen, ibuprofen, calcium carbonate, magnesium hydroxide, magnesium carbonate, magnesium oxide, aluminum hydroxide, mixtures thereof, and pharmaceutically acceptable salts thereof.

The active ingredient comprises at least 60 weight percent of the uncoated, compressed tablet. Preferably, the active ingredient comprises at least about 75 weight percent of the tablet. More preferably, the active ingredient comprises at least about 85 weight percent of the tablet. The tablet may comprise more than one active ingredient, in which case the sum of the weights of the active ingredients is at least 60, preferably at least about 75, more preferably at least about 85, weight percent of the tablet. (Optionally, the tablet may be coated with one or more outer coatings as discussed below. However, the amount of active ingredient is expressed as a weight percent of the uncoated tablet.)

The particle size of the active ingredient may vary over a wide range. Specifically, the particle size may range from about 50 to about 150 microns, or from about 150 to about 500 microns, or from about 500 to about 650 microns.

The tablet may be designed for swallowing, chewing, or dissolving in the mouth. In the case of chewable or orally dispersible tablets, if the active ingredient has an objectionable taste, it may typically be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked active ingredients may also be employed. For example, acetaminophen particles which are encapsulated with ethylcellulose or other polymers by a coaccervation process may be used in the present invention. Coaccervation-encapsulated acetaminophen may be purchased commercially from Eurand America, Inc. Vandalia, Ohio, or from Circa Inc., Dayton, Ohio.

Examples of suitable powdered waxes include linear hydrocarbons such as polyalkalene waxes; other waxes such as shellac wax, microcrystalline wax, paraffin-type waxes, polyalkalene glycols, Carnauba wax, spermaceti wax, beeswax, candelilla wax, polyethylene oxides, hydrogenated vegetable oils, synthetic polyethylene waxes, and derivatives and mixtures thereof. In one embodiment, the powdered wax is selected from polyethylene wax, microcrystalline wax, and mixtures thereof. In another embodiment, the powdered wax is selected from shellac wax, paraffin-type waxes, polyethylene glycol, and mixtures thereof. In one embodiment the powdered wax is polyethylene wax.

The wax preferably comprises up to about 20 weight percent of the tablet. More preferably, the wax comprises about 1 to about 10 weight percent of the tablet. Most preferably, the wax comprises about 2 to about 8 weight percent of the tablet.

The wax is present in solid, powdered form. Preferably, the average particle size of the wax is in the range of about 5 to about 100 microns, more preferably about 10 to about 40 microns. We have discovered that long chain hydrocarbons having a chain length of 40 carbons or greater, i.e. a chain length of 60 carbons or greater, are most suitable for use in this invention. The waxes useful in this invention typically have a melting point greater than about 90° C., i.e. at least about 95° C., or from about 100° C. to 125° C. Linear, or straight chain, hydrocarbons are preferred in this invention due to their higher melting temperature compared to non-linear, or branched, hydrocarbons of a similar carbon number. Synthetically produced hydrocarbons are preferred due to their purity of linearity and chain length, which results in a sharp and reproducible melting point from lot to lot.

The tablet may contain other conventional ingredients such as fillers, including water soluble compressible carbohydrates such as sucrose, mannitol, sorbitol, maltitol, xylitol, erythritol, lactose, and mixtures thereof; conventional dry binders including cellulose, cellulosic derivatives, polyvinyl pyrrolidone, starch, modified starch, and mixtures thereof, and in particular microcrystalline cellulose; sweeteners including aspartame, acesulfame potassium, sucralose and saccharin; disintegrants such as microcrystalline cellulose, starch, sodium starch glycolate, crosslinked polyvinylpyrrolidone, crosslinked carboxymethylcellulose; and lubricants, such as magnesium stearate, stearic acid, talc, and waxes. The tablet may also incorporate pharmaceutically acceptable adjuvants, including for example preservatives, flavors, acidulants, antioxidants, glidants, surfactants, and coloring agents. Typically the total amount of these other conventional ingredients will not exceed about 25 percent of the tablet weight, i.e. not more than about 20 percent of the tablet weight, or not more than about 15 percent of the tablet weight.

Tablets of the present invention may be made by any means known in the art. Conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are known in the art, and are described in detail in, for example, Lachman, et al., "The Theory and Practice of Industrial Pharmacy," Chapter 11, ($3^{rd}$ Ed. 1986), which is incorporated by reference herein.

Preferably the tablets are formed by the direct compression method, which involves directly compacting a blend of the active ingredient, the powdered wax, and any other appropriate optional ingredients. After blending, a pre-determined volume of the powder blend is filled into a die cavity of a rotary tablet press, which continuously rotates as part of a "die table" from the filling position to a compaction position. The powder blend is compacted between an upper punch and a lower punch to an ejection position, at which the resulting tablet is pushed from the die cavity by the lower punch and guided to an ejection chute.

The direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, and the like, which can have an adverse effect on dissolution.

In embodiments wherein a swallowable tablet is desired, the degree of particle compaction is controlled so that the resulting tablets have a hardness of about 1 to 30 kiloponds per square centimeter ($kp/cm^2$). "Hardness" is a term used in the art to describe the diametrical breaking strength as measured by conventional pharmaceutical hardness testing equipment, such as a Schleuniger Hardness Tester. In order to compare values across different size tablets, the breaking strength is normalized for the area of the break (which may be approximated as the tablet diameter times the thickness). This normalized value, expressed in $kp/cm^2$, is sometimes referred in the art as tablet tensile strength. A general discussion of tablet hardness testing is found in Leiberman et al., *Pharmaceutical Dosage Forms—Tablets*, Volume 2, $2^{nd}$ ed., Marcel Dekker Inc., 1990, pp. 213-217, 327-329 (hereinafter "Lieberman").

In one embodiment of the invention, the tablet has a hardness in the range of about 4 to 20 $kp/cm^2$. The tablet of this embodiment may or may not comprise an outer coating as described below. In another embodiment, the tablet preferably has a hardness in the range of about 10 to 20 $kp/cm^2$.

In a preferred embodiment of the invention, the tablet is relatively soft, having a hardness in the range of about 1 to 4 kp/cm2. In this embodiment, the tablet is made using a novel compression process and apparatus, which is described in commonly assigned, copending U.S. application Ser. No. 09/966,509 filed Sep.28, 2001.

Optionally, one or more outer coatings may be applied over the tablet to provide protection during packaging and handling. Such outer coatings comprise one or more tablet coating materials, such as gelatin, isomalt, monosaccharides, disaccharides, polysaccharides such as starch, cellulose derivatives, shellacs, polyhedric alcohols such as xylitol, mannitol, sorbitol, maltitol, erythritol, polyalkylene glycols, and the like. A variety of such outer coatings are known in the art, and any of these may be employed using techniques also known in the art.

Even uncoated, however, the present tablet advantageously has acceptable friability. In the embodiment of the invention wherein the tablet hardness ranges from about 4 to 20 $kp/cm^2$, friability levels are typically less than about 2%, preferably less than about 1%. A discussion of tablet friability is presented in USP 23 (1995) <1216>p. 1981.

The tablet of the invention is an immediate release dosage form. Specifically, the tablet meets the USP dissolution specifications for immediate release tablets containing the particular active ingredient in the tablet. This surprising in view of the teachings in the art, see for example U.S. Pat. No. 4,882,167 to Jang (discussed above). This is also surprising in view of the fact that the tablet contains wax, a hydrophobic material.

In an alternative embodiment of the invention, the tablet comprises an insert embedded inside it. Such an insert may have any composition desired and preferably comprises additional active ingredient. For example, such additional active ingredient may be different from the active ingredient in the tablet proper. Alternatively, the additional active ingredient may be the same chemical entity as the active ingredient in the tablet, but have a different release profile, i.e., a controlled release or extended release profile. In one embodiment, the active ingredient in the insert is a high potency active ingredient, for example loratadine, fexofenadine, cetirizine, chlorpheniramine, brompheniramine, diphenhydramine, pseudoephedrine, cyproheptadine, montelukast, loperamide, famotidine, dexamethasone, hydrocortisone, cyclobenzaprine, alendronate, hydrochlorthiazide, rofecoxib, indomethacin, ketoprofen, meloxicam, piroxicam, lovastatin, atorvastatin, pravastatin, simvastatin, finasteride, and pharmaceutically acceptable salts, esters, and mixtures thereof.

Preferably, the insert is a solid material. It may be produced and embedded in the tablet by methods known in the art. For example the insert may be made by direct compression, followed by compression of the remaining tablet ingredients (as a powder) around the insert. Alternatively, the insert may be made using a thermal setting molding module as described in commonly assigned, copending U.S. Application Ser. No. 09/966,450 filed Sept. 28, 2001. In particular, a starting material in flowable form, for example comprising a thermal setting polymer and an active ingredient, is introduced into a molding chamber within the thermal setting molding module. The starting material is cooled and solidified within the chamber. It is then transferred into a volume of powder comprising the remaining tablet ingredients, which are compressed around the insert.

Suitable thermal setting polymers include any edible material that is flowable at a temperature between about 37° C. and about 120° C., and that is solid at a temperature between about 0° C. and about 35° C. Preferred thermal setting polymers include water-soluble polymers such as polyalkylene glycols, polyethylene oxides and derivatives, and sucrose esters; fats such as cocoa butter, hydrogenated vegetable oil such as palm kernel oil, cottonseed oil, sunflower oil, and soybean oil; mono- di- and triglycerides, phospholipids, linear hydrocarbons such as polyethylene wax, waxes such as Carnauba wax, spermaceti wax, beeswax, candelilla wax, shellac wax, microcrystalline wax, and paraffin wax; fat-containing mixtures such as chocolate; sugar in the form on an amorphous glass such as that used to make hard candy forms, sugar in a supersaturated solution such as that used to make fondant forms; low-moisture polymer solutions such as mixtures of gelatin and other hydrocolloids at water contents up to about 30% such as those used to make "gummi" confection forms. In a particularly preferred embodiment, the thermal setting polymer is a water-soluble polymer such as polyethylene glycol.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example 1

Tablets according to the invention were prepared as follows. The following ingredients were mixed well in a plastic bag: 180.5 g acetaminophen USP (APAP, 500 mg/tablet) and 20.9 g of microcrystalline wax powder (60 mg/tablet). Next, 4.18 g of sodium starch glycolate (EXPLOTAB) (12 mg/tablet) were added to the bag, and mixed well. Then 0.70 g of magnesium stearate NF (2 mg/tablet) were added to the bag, and the ingredients were again mixed. The resulting granulation was compressed into tablets on a Betapress with 7/16 inch extra deep concave tooling.

The resulting tablets had approximate weights of 574 mg, thicknesses of 0.284 inches, and hardness of 3.6 kp. The dissolution data for the tablets is shown below.

|  | APAP Dissolution in pH 5.8 buffer | |
| --- | --- | --- |
|  | 15 min | 30 min |
| Initial | 101.57 | 101.77 |
| 4 wk 40/75 | 97.83 | 102.33 |
| 12 wk 40/75 | 80.77 | 102.63 |

Example 2

Tablets according to the invention were prepared as follows. The following ingredients were mixed well in a plastic bag: 174.5 g acetaminophen USP (APAP, 500 mg/tablet) and 20.9 g of hydrogenated vegetable oil powder (Sterotex) (60 mg/tablet). Next, 4.19 g of sodium starch glycolate (EXPLOTAB) (12 mg/tablet) were added to the bag, and mixed well. Then 0.35 g of magnesium stearate NF (1 mg/tablet) were added to the bag, and the ingredients were again mixed. The resulting granulation was compressed into tablets on a Betapress with 7/16 inch extra deep concave tooling.

The resulting tablets had approximate weights of 573 mg, thicknesses of 0.281 inches, and hardness of 2 kp. The dissolution data for the tablets is shown below.

|  | APAP Dissolution in pH 5.8 buffer | |
| --- | --- | --- |
|  | 15 min | 30 min |
| Initial | 101.70 | 101.93 |
| 1 wk 50 C | 100.30 | 101.33 |
| 2 wk 50 C | 99.33 | 101.03 |
| 2 wk 40/75 | 98.43 | 100.57 |
| 4 wk 40/75 | 97.00 | 101.17 |

Example 3

Tablets according to the invention were prepared as follows. The following ingredients were mixed well in a plastic bag: 130.9 g acetaminophen USP (APAP, 500 mg/tablet) and 15.7 g of glyceryl behenate powder(Compritol 888) (60 mg/tablet). Next, 3.14 g of sodium starch glycolate (EXPLOTAB) (12 mg/tablet) were added to the bag, and mixed well. Then 0.26 g of magnesium stearate NF (1 mg/tablet) were added to the bag, and the ingredients were again mixed. The resulting granulation was compressed into tablets on a Betapress with 7/16 inch extra deep concave tooling.

The resulting tablets had approximate weights of 573 mg, thicknesses of 0.281 inches, and hardness of 2.2 kp. The dissolution data for the tablets is shown below.

| | APAP Dissolution in pH 5.8 buffer | |
|---|---|---|
| | 15 min | 30 min |
| Initial | 101.17 | 102.53 |
| 1 wk 50 C | 95.53 | 101.70 |
| 2 wk 50 C | 91.13 | 102.30 |
| 2 wk 40/75 | 93.43 | 102.43 |
| 4 wk 40/75 | 94.83 | 102.67 |

Example 4

Tablets according to the invention were prepared as follows. The following ingredients were mixed well in a plastic bag: 109.8 g acetaminophen USP (APAP, 500 mg/tablet) and 11.0 g of synthetic wax X-1133 T6 (50 mg/tablet). Next, 3.30 g of sodium starch glycolate (EXPLOTAB) (15 mg/tablet) and 0.22 g of silicon dioxide (1 mg/tablet) were added to the bag, and mixed well. Then 0.66 g of magnesium stearate NF (3 mg/tablet) were added to the bag, and the ingredients were again mixed. The resulting granulation was compressed into tablets on a Betapress with 7/16 inch extra deep concave tooling.

The resulting tablets had approximate weights of 569 mg, thicknesses of 0.276 inches, and hardness of 3.9 kp. The dissolution data for the tablets is shown below.

| | APAP Dissolution in pH 5.8 buffer | |
|---|---|---|
| | 15 min | 30 min |
| Initial | 101.33 | 102.33 |
| 1 wk 40/75 | 99.03 | 101.57 |
| 1 wk 50 C | 101.10 | 102.07 |
| 2 wk 40/75 | 98.87 | 101.00 |
| 2 wk 50 C | 94.90 | 100.77 |
| 12 wk 40/75 | 99.87 | 101.70 |

Example 5

A tablet is made according to Example 1, except the tablet contains an insert embedded in the center thereof. The insert comprises pseudoephedrine HCl and polyethylene glycol.

The insert is made using a thermal setting molding module comprising a molding chamber as described in commonly assigned, copending U.S. application Ser. No. 09/966,450 filed Sept. 28, 2001. Starting material comprising a mixture of pseudoephedrine HCl and molten polyethylene glycol is fed to the molding chamber. The starting material is cooled and solidified within the molding chamber. It is then transferred to the mixture of tablet ingredients prior to compression in the Betapress.

We claim:

1. A swallowable immediate release tablet consisting essentially of at least 60 weight % of acetaminophen, from about 1 to about 10 weight % of a powdered wax having an melting point greater than about 90° C. and a particle size in the range of about 5 to about 100 microns, and less than about 25 weight % of a disintegrant, wherein the acetaminophen is released from the swallowable immediate release tablet by 30 minutes in pH 5.8 buffer.

2. The tablet of claim 1, wherein the wax is selected from the group consisting of linear hydrocarbons, microcrystalline wax, and mixtures thereof.

3. The tablet of claim 1 prepared by direct compression.

4. The tablet of claim 1 which is substantially free of water-soluble, non-saccharide polymeric binders.

5. The tablet of claim 1, which is substantially free of hydrated polymers.

6. The tablet of claim 1 further comprising an excipient selected from the group consisting of flow aids, and lubricants.

7. A swallowable immediate release tablet consisting essentially of at least 60 weight percent of acetaminophen, from about 1 to about 10 weight % of a powdered wax having a particle size in the range of about 5 to about 100 microns that is selected from the group consisting of shellac wax, paraffin-type waxes, polyethylene glycol, and mixtures thereof, and less than about 25 weight % of a disintegrant, wherein said swallowable immediate release tablet is prepared by direct compression, and the acetaminophen is released from the swallowable immediate release tablet by 30 minutes in pH 5.8 buffer.

8. A swallowable immediate release tablet consisting essentially of at least 60 weight percent of acetaminophen, from about 1 to about 10 weight % of a powdered wax having a particle size in the range of about 5 to about 100 microns that is selected from the group consisting of shellac wax, paraffin-type waxes, polyethylene glycol, and mixtures thereof, and less than about 25 weight % of a disintegrant, wherein said swallowable immediate release tablet is substantially free of water-soluble, non-saccharide polymeric binders, and the acetaminophen is released from the swallowable immediate release tablet by 30 minutes in pH 5.8 buffer.

9. A swallowable immediate release tablet consisting essentially of at least 60 weight percent of acetaminophen, from about 1 to about 10 weight % of a powdered wax having a particle size in the range of about 5 to about 100 microns that is selected from the group consisting of shellac wax, paraffin-type waxes, polyethylene glycol, and mixtures thereof, and less than about 25 weight % of a disintegrant, wherein said swallowable immediate release tablet is substantially free of hydrated polymers, and the acetaminophen is released from the swallowable immediate release tablet by 30 minutes in pH 5.8 buffer.

* * * * *